United States Patent
Panian et al.

(10) Patent No.: US 9,872,977 B2
(45) Date of Patent: Jan. 23, 2018

(54) PISTON FOR A NEEDLELESS VALVE SYSTEM

(71) Applicant: CareFusion 303, Inc., San Diego, CA (US)

(72) Inventors: Tyler Devin Panian, Long Beach, CA (US); Jonathan Yeh, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 14/458,116

(22) Filed: Aug. 12, 2014

(65) Prior Publication Data

US 2014/0358073 A1 Dec. 4, 2014

Related U.S. Application Data

(63) Continuation of application No. 13/355,037, filed on Jan. 20, 2012, now Pat. No. 8,801,678.

(51) Int. Cl.
*A61M 39/20* (2006.01)
*A61M 39/26* (2006.01)
*F16J 1/01* (2006.01)
*A61M 5/30* (2006.01)
(Continued)

(52) U.S. Cl.
CPC .............. *A61M 39/20* (2013.01); *A61M 5/30* (2013.01); *A61M 39/26* (2013.01); *B05B 9/0413* (2013.01); *F16J 1/01* (2013.01); *A61M 2039/0009* (2013.01); *A61M 2039/0036* (2013.01); *A61M 2039/0072* (2013.01); *Y10T 137/0318* (2015.04)

(58) Field of Classification Search
CPC ........ A61M 39/20; A61M 5/30; A61M 39/26; A61M 2039/0009; A61M 2039/0036; A61M 2039/0072; B05B 9/0413; F16J 1/01; Y10T 137/0318
See application file for complete search history.

(56) References Cited

U.S. PATENT DOCUMENTS

| | | |
|---|---|---|
| 5,203,775 A | 4/1993 | Frank et al. |
| 5,289,849 A | 3/1994 | Paradis |
| 5,465,938 A | 11/1995 | Werge et al. |

(Continued)

FOREIGN PATENT DOCUMENTS

| | | |
|---|---|---|
| JP | H07285854 A | 10/1995 |
| JP | 2007175477 A | 7/2007 |

(Continued)

OTHER PUBLICATIONS

Extended European Search Report for Application No. 13738743.7, dated Jul. 1, 2015, 6 pages.

(Continued)

*Primary Examiner* — Emily Schmidt
*Assistant Examiner* — Lauren M Peng
(74) *Attorney, Agent, or Firm* — McDermott Will & Emery LLP

(57) ABSTRACT

A piston for a needleless valve system comprising a head portion configured to be disposed in the needleless valve system and controlling fluid flow through the needleless valve system. The head portion comprising a continuous top surface, and an opening disposed proximate the continuous top surface, wherein the continuous top surface is non-planar when the opening is in an open position.

20 Claims, 5 Drawing Sheets

(51) Int. Cl.
*B05B 9/04* (2006.01)
*A61M 39/00* (2006.01)

(56) References Cited

U.S. PATENT DOCUMENTS

| | | |
|---|---|---|
| 5,569,235 A | 10/1996 | Ross et al. |
| 5,601,207 A | 2/1997 | Paczonay |
| 5,676,346 A | 10/1997 | Leinsing |
| 5,749,861 A | 5/1998 | Guala et al. |
| 6,804,656 B1 | 10/2004 | Rosenfeld et al. |
| D507,447 S | 7/2005 | Moore et al. |
| 7,207,945 B2 | 4/2007 | Bardy |
| 7,591,449 B2 | 9/2009 | Raines et al. |
| 7,959,574 B2 | 6/2011 | Bardy |
| 2002/0133124 A1 | 9/2002 | Leinsing et al. |
| 2006/0276757 A1* | 12/2006 | Fangrow, Jr. ......... A61M 39/02 604/247 |
| 2007/0233046 A1* | 10/2007 | Funamura ........... A61M 39/223 604/535 |
| 2009/0105666 A1 | 4/2009 | Peppel |
| 2011/0130724 A1 | 6/2011 | Mansour et al. |

FOREIGN PATENT DOCUMENTS

| | | |
|---|---|---|
| WO | 1998026835 | 6/1998 |
| WO | 2011060384 | 5/2011 |

OTHER PUBLICATIONS

International Preliminary Report on Patentability in PCT Application No. PCT/US2013/021674 dated Jul. 22, 2014.
International Search Report and Written Opinion for PCT/US2013/021674 dated Apr. 29, 2013.
Australian Patent Examination Report No. 1 for Application No. 2013209931, dated Oct. 10, 2016, 5 pages.
Japanese Office Action for Application No. 2014-553357, dated Nov. 1, 2016, 3 pages excluding English translation.
Japanese Office Action for Application No. 2014-553357, dated Jun. 13, 2017, 3 pages excluding translation.
Australian Examination Report No. 2 for Application No. 2013209931, dated Feb. 1, 2017, 3 pages.

* cited by examiner

500

```
┌─────────────────────────────────────────────────────────────┐
│ SEAL A PORT OF A HOUSING WITH A CONTINUOUS TOP SURFACE,     │
│ WHEREIN THE CONTINUOUS TOP SURFACE IS PLANAR WHEN THE       │
│ PORT IS SEALED, WHEREIN A CHANNEL DISPOSED PROXIMATE THE    │
│ CONTINUOUS TOP SURFACE IS COMPRESSED IN A CLOSED POSITION   │
│                            510                              │
└─────────────────────────────────────────────────────────────┘
                              ↓
┌─────────────────────────────────────────────────────────────┐
│     DEPRESS THE CONTINUOUS TOP SURFACE BY A NEEDLELESS      │
│                          DEVICE                             │
│                            520                              │
└─────────────────────────────────────────────────────────────┘
                              ↓
┌─────────────────────────────────────────────────────────────┐
│     OPEN THE CHANNEL SUCH THAT THE CONTINUOUS TOP SURFACE   │
│                        IS NON-PLANAR                        │
│                            530                              │
└─────────────────────────────────────────────────────────────┘
                              ↓
┌─────────────────────────────────────────────────────────────┐
│     ALLOW FLUID TO FLOW AROUND THE NON-PLANAR CONTINUOUS    │
│                          TOP SURFACE                        │
│                            540                              │
└─────────────────────────────────────────────────────────────┘

┌─────────────────────────────────────────────────────────────┐
│        INJECT FLUID THOUGH THE PORT VIA THE NEEDLELESS      │
│                            DEVICE                           │
│                            550                              │
└─────────────────────────────────────────────────────────────┘

┌─────────────────────────────────────────────────────────────┐
│   RESEAL THE PORT WITH THE CONTINUOUS TOP SURFACE IN        │
│   RESPONSE TO REMOVING THE NEEDLELESS DEVICE FROM THE PORT  │
│                            560                              │
└─────────────────────────────────────────────────────────────┘
```

FIG. 5

PISTON FOR A NEEDLELESS VALVE SYSTEM

This application is a Continuation of application Ser. No. 13/355,037, filed on Jan. 20, 2012, U.S. Pat. No. 8,801,678. The entire content of this application is incorporated by reference herein.

BACKGROUND

Needleless devices or connectors are utilized as an alternative to hypodermic needles. Needleless connectors are utilized as fluid ports for a catheter attached to a patient. As a result of not using needles, needleless connectors reduce the risk of acquiring bloodborne diseases.

However, needleless connectors may contain surfaces and features that are difficult to clean. For example, some needleless connectors include a "split septum" (e.g., slit, cut, pathway, etc.) on a top surface of a piston or valve plug. Typically, the split septum is unable to be properly swabbed after use. Accordingly, pathogens may be present in the unsanitized areas which may lead to patient infection.

BRIEF DESCRIPTION OF THE DRAWINGS

FIG. 5 illustrates an embodiment of a method for flow control in a needleless valve system.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
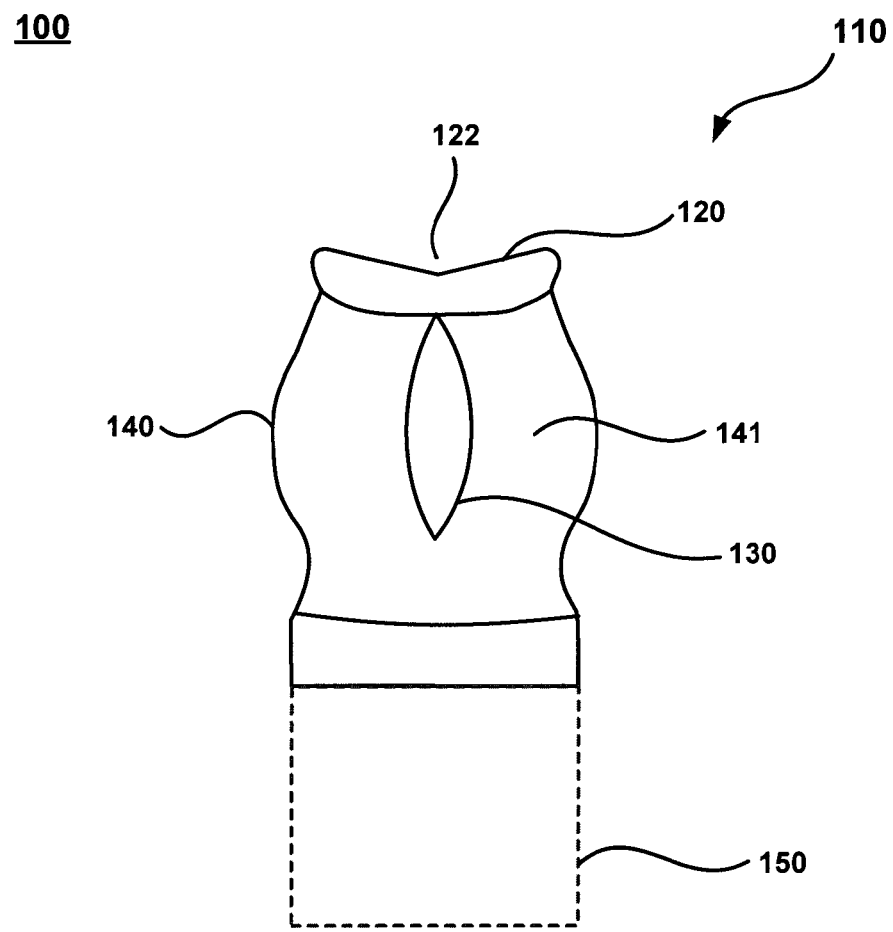
FIG. 1 illustrates an embodiment of a piston.

FIG. 1 depicts an embodiment of piston 100 which is configured to be disposed in a needleless valve system. The structure and function of the needleless valve system will be described in detail further below.

Piston 100 includes head portion 110 and base portion 150. In various embodiments, base portion 150 can be any physical structure that facilitates in head portion 110 controlling the flow of fluid through the needleless valve system. As such, base portion 150 is generically depicted as a simple square with dotted lines. Accordingly, the focus of the description herein will focus primarily on the structure and functionality of head portion 110 with respect to a needleless valve system.

Head portion 110 includes continuous top surface 120, opening 130 and compression features 140 and 141.

Continuous top surface 120 is configured to seal a port of a housing, which will be described in detail below. Continuous top surface 120 does not include (or does not require) any broken portions. For example, continuous top surface 120 is a continuous feature that does not include a slit, cut, hole, etc.

Continuous top surface 120 is a smooth surface. Accordingly, when continuous top surface 120 is swabbed, pathogens are readily removed and continuous top surface 120 is properly sanitized.

Continuous top surface 120 is non-planar in the relaxed state of head portion 110. This is based, in part, on opening 130 being in a relaxed open position, as depicted in FIG. 1. A relaxed state is understood as the natural physical position of head portion 110 without any forces applied to head portion 110.

In one example, continuous top surface 120 includes non-planar configuration of a trough 122 in the relaxed state. It should be understood that the non-planar configuration can be any non-planar configuration that is conducive to allowing fluid flow around continuous top surface 120. Examples of non-planar configurations can be, but are not limited to, a concave surface, a valley, cavity, etc.

In one embodiment, head portion 110 is cylindrical. Thus, continuous top surface 120 is circular.

Opening 130 is disposed proximate continuous top surface 120. Opening 130 is in an open position when head portion 110 is in a relaxed state, as described above.

Opening 130 can be compressed to a closed position. For example, when head portion 110 is laterally compressed, then opening 130 is also laterally compressed to a closed position. In other words, the outer surface or walls of head portion is compressed inwards until opening 130 is closed. As a result, continuous top surface 120 is deformed into a planar surface.

Opening 130 can be any physical feature (e.g., hollow, void, channel, etc.) disposed in any orientation within head portion 110 and is able to resiliently open and close. Moreover, opening can be any shape that facilitates in allowing head portion 110 to deform such that continuous top surface 120 is deformed into a planar surface. For example, shapes of opening 130 can be, but is not limited to elliptical, oval, diamond, circle, etc.

Opening 130 is enclosed within head portion 110. For example, the periphery (or side surfaces) of opening 130 is fully enclosed within head portion 110.

In one embodiment, opening 130 is disposed along a diameter of head portion 110. In another embodiment, opening 130 is centrally disposed along a center axis of head portion 110. In various embodiments, opening 130 is disposed in any location that enables the deformation of continuous top surface 120.

Compression features 140 and 141 are disposed on the periphery of head portion 110. Compression features 140 and 141 are configured to facilitate in engaging with a housing such that opening 130 is compressed in a closed position.

In one embodiment, compression features 140 and 141 are bulges. It should be understood that compression features can be any physical features that facilitates in the engaging of a housing such that opening 130 is compressed in a close position.

Figure 2:
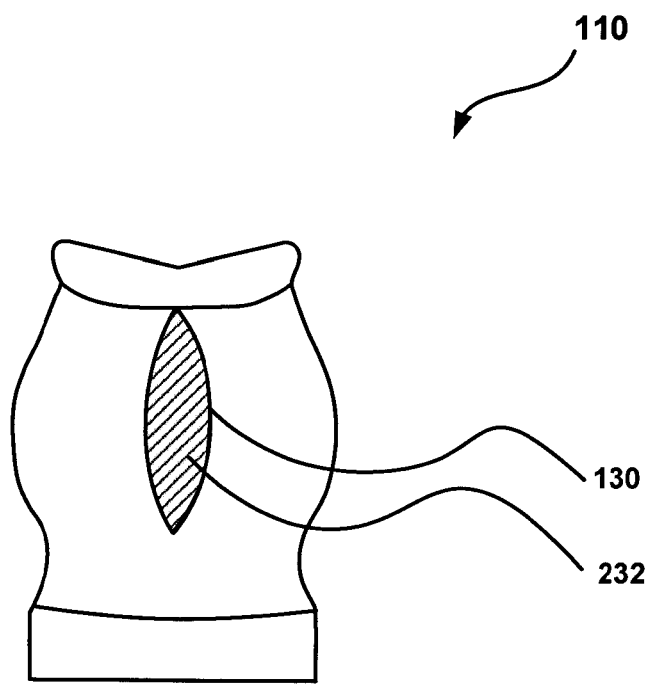
FIG. 2 illustrates an embodiment of a head portion of a piston.

FIG. 2 depicts an embodiment of spacer 232 disposed in opening 130. Spacer 232 is configured to facilitate in the resilient opening of opening 130 from a closed position to an open position. Spacer 232 is depicted in a relaxed or natural position. However, spacer 232 can be fully compressed when opening 130 is in the closed position. It should be understood that spacer 232 can be any resiliently compressible material. Moreover, spacer 232 can be any shape disposed in any orientation within opening 130 to facilitate in the resilient opening of opening 130 from a closed position to an open position.

Figure 3:
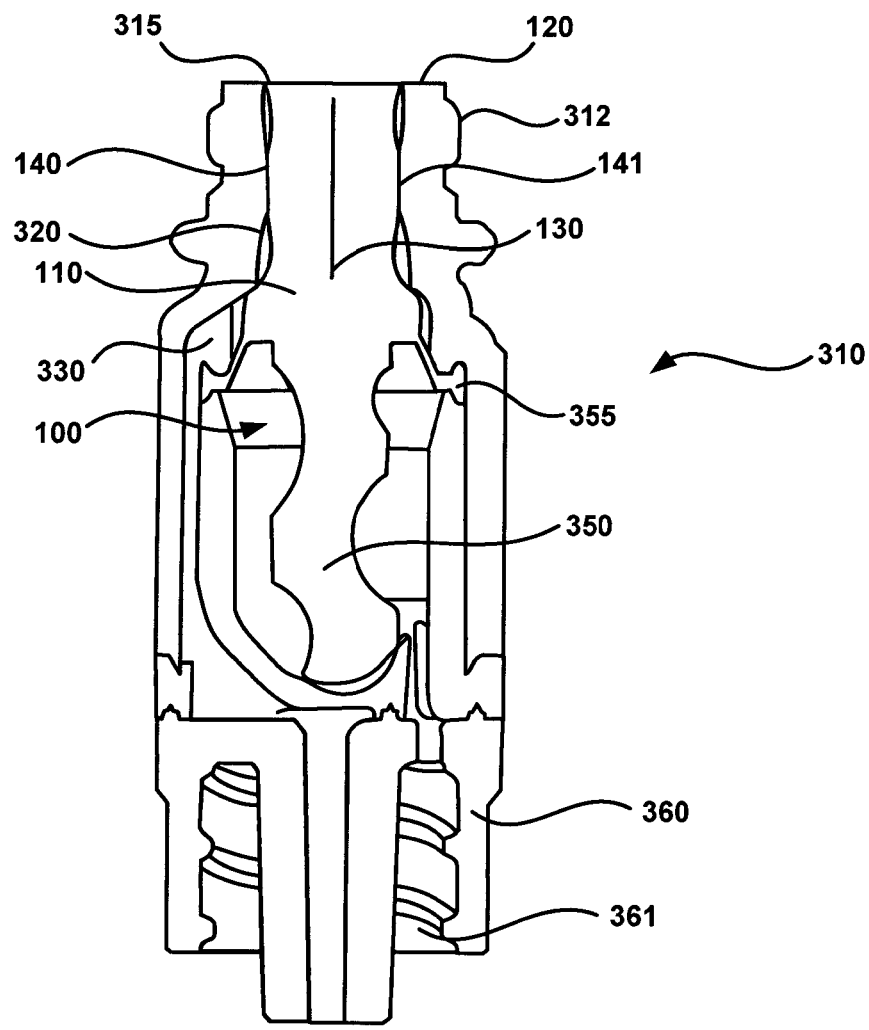
FIGS. 3 and 4 illustrate embodiments of a needleless valve system.
Figure 4:
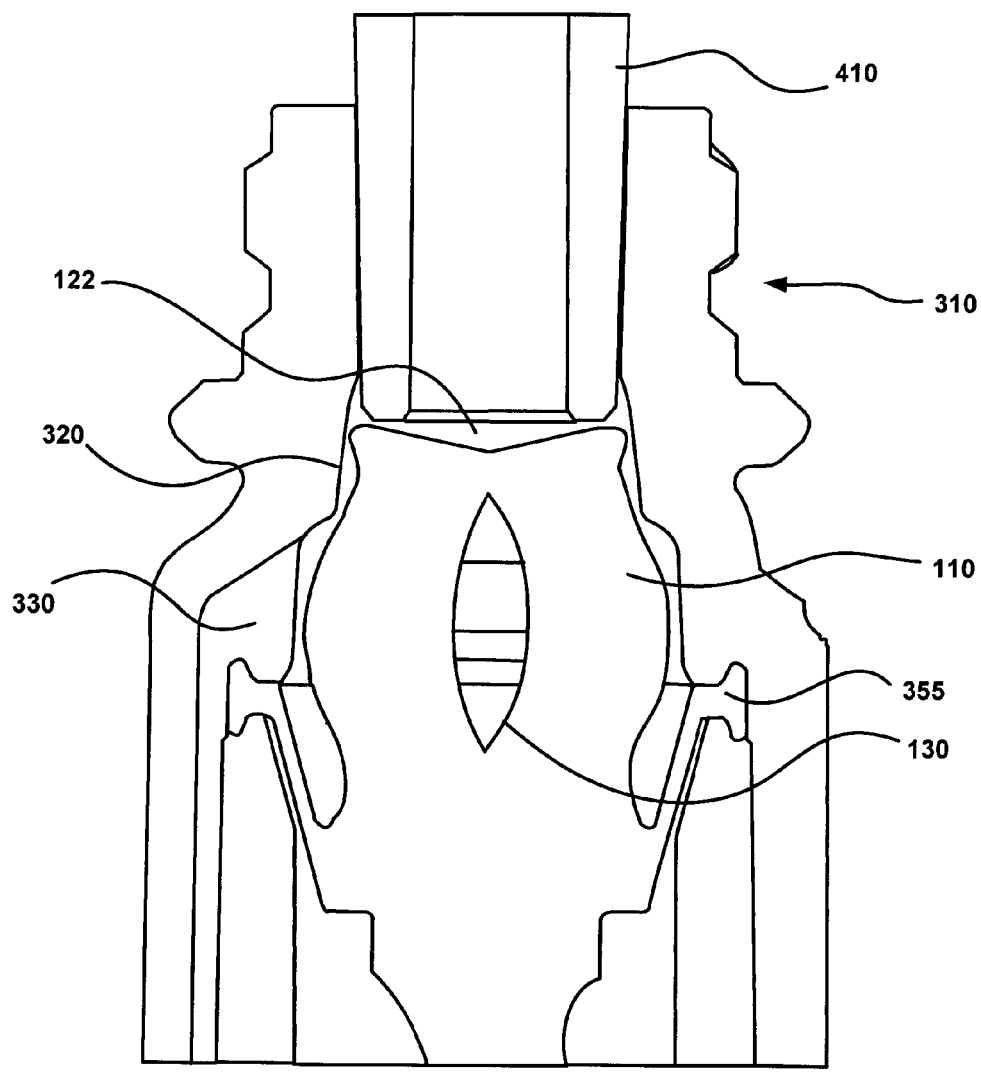

FIGS. 3 and 4 depict embodiments of needleless valve system 300. In general, needleless valve system 300 is configured to be coupled with medical devices (e.g., a catheter) and convey fluid without the use of a needle.

Needleless valve system 300 includes piston 100 disposed in housing 310. Housing 310 includes port 315, inner wall 320, and base 360.

Needleless valve system 300 is initially sealed, as depicted in FIG. 3. In particular, piston 100 is seated in housing 310 such that port 315 is fluidly sealed by head portion 110. Additionally, the outer diameter of head portion 110 is compressed and seated within inner wall 320 to create a seal.

Opening 130 is compressed in a close position which results in continuous top surface 120 to be deformed into a planar surface. As a result, port 315 is sealed by continuous top surface 120 because the periphery of continuous top surface 120 mates with port 315.

In one embodiment, needleless valve system 300 is fluidly connected to a catheter. For example, female luer fitting 361 of base 360 is connected to a catheter. Accordingly, fluid flow is able to flow to/from the catheter.

FIG. 4 depicts needleless valve system 300 in an open position due to tip 410 of a needleless syringe being inserted into needleless valve system 300. Tip 410 displaces head portion 110 downward along inner wall 320. In one embodiment, housing 310 includes a male luer fitting 312 that corresponds to a female luer fitting of the syringe.

The diameter of inner wall 320 increases in the downward direction. Accordingly, the diameter of head portion 110 also increases when moving in the downward direction. Thus, opening 130 subsequently expands into its natural open position.

Moreover, continuous top surface 120 is deformed from planar to non-planar to create trough 122. Therefore, fluid is able to flow around continuous top surface 120 via trough 122 to volume 330. The fluid then flows from volume 330 through base 360 to a medical device, such as a catheter.

In one embodiment, fluid is able to flow in the opposite direction. For example, blood flows from a patient into volume 330 around continuous top surface 120 via trough 122 and into the syringe.

In various embodiments, it should be appreciated that needleless valve system 300 can allow positive and/or negative fluid displacement.

Piston 100 is an elastic body. As such, piston 100 is able to deform back to its original position such that head portion 110 is pushed up through inner wall 320. Accordingly, head portion is compressed against inner wall 320 and port 315 is subsequently sealed.

In particular, base portion 350 acts as a spring to facilitate in opening 130 deforming to a closed position and head portion 110 resealing port 315. For example, base portion 350 includes a tail that resiliently deforms to its original position in response to tip 410 being removed from housing 310. The spring force of base portion 350 causes head portion 110 to move upward within inner wall 320 and head portion 110 is compressed within inner wall 320. As a result, opening 310 is deformed into a closed position and continuous top surface 120 is deformed into a planar surface. Moreover, the spring force of the diaphragm 355 also causes head portion 110 to move in and be compressed within inner wall 320.

Additionally, compression features 140 and 141 (e.g., bulges) enhance the compression of head portion 110 within housing 310. Compression features 140 and 141 increase the diameter of head portion 110 and thus, increase the forces applied on head portion 110 to close opening 130.

It should be appreciated that base portion 350 can include any elastic feature for generating a spring force to translate head portion 110 within inner wall 320 such that port 315 is resealed.

In various embodiments, a base portion (e.g., base portion 150 or base portion 350) can include any combination of a tale and/or a diaphragm. In one embodiment, a base portion does not include a tale and/or a diaphragm.

Oftentimes pathogens may be present on or around continuous top surface 120 after tip 410 of the syringe is removed from needleless valve system 300. However, the pathogens are easily swabbed away from the smooth continuous top surface. Therefore, the risk of patient infection is reduced.

FIG. 5 depicts an embodiment of a method 500 for controlling fluid flow. In some embodiments, method 500 is performed at least by needleless valve system 300, as depicted in FIGS. 3 and 4.

At 510 of method 500, a port of a housing is sealed with a continuous top surface. The continuous top surface is planar when the port is sealed, and a channel disposed proximate continuous top surface is compressed in a closed position. For example, port 315 is fluidly sealed with continuous top surface 120 when continuous top surface 120 is planar. Moreover, opening 130 (e.g. a channel) is disposed proximate continuous top surface 120 and is collapsed or compressed.

At 520, the continuous top surface is depressed by a needleless device. For example, continuous top surface 120 is depressed down through housing 310 by tip 410 of a needleless syringe.

At 530, the channel is opened such that the continuous top surface is non-planar. For example, when head portion 110 slides down through housing 310, opening 130 expands to a natural open position.

At 540, in response to the opening the channel, fluid is allowed to flow around the non-planar continuous top surface. For example, opening 130 expands to a natural open position which causes continuous top surface 120 to bend or fold to create trough 122. As a result, fluid is allowed to flow around non-planar continuous top surface 120 through housing 310.

At 550, fluid is injected through the port via the needleless device. For example, medicine is injected through port 315 via a fluid channel of tip 410 of a needleless syringe.

At 560, the port is resealed with the continuous top surface in response to removing the needleless device from the port. For example, tip 410 is removed from housing 310. In response, as head portion 110 is compressed within inner wall 320, opening 130 is compressed to a closed position and continuous top surface 120 is deformed to a planar state and thus, port 315 is fluidly sealed.

Various embodiments of the present invention are thus described. While the present invention has been described in particular embodiments, it should be appreciated that the present invention should not be construed as limited by such embodiments, but rather construed according to the following claims.

The invention claimed is:

1. A piston for a needleless valve system, the piston comprising:
    a head portion having a continuous top surface and compression features; wherein, when the head portion is in a relaxed state, the top surface being non-planar and the compression features separated to form an opening adjacent the top surface, and when the compression features are pressed together to close the opening between the compression features, the top surface being substantially planar.

2. The piston of claim 1, wherein the top surface comprises a depression when the head portion is in a relaxed state.

3. The piston of claim 2, wherein the depression comprises a trough.

4. The piston of claim 1, wherein the opening comprises an elliptical, an oval, or a diamond shape.

5. The piston of claim 1, wherein the opening passes through the head portion.

6. The piston of claim 5, wherein the opening extends along a diameter of the head portion.

7. The piston of claim 6, wherein the opening is centrally disposed along a center axis of the head portion.

8. The piston of claim 1, wherein the compression features are disposed along a circumference of the head portion.

9. The piston of claim 8, wherein the compression feature comprises a bulge.

10. A needleless valve system comprising:
    a housing comprising a fluid port; and
    a piston comprising a head portion having a continuous top surface and compression features, the top surface being non-planar and the compression features separated to form an opening adjacent the top surface when the head portion is in a relaxed state, and the top surface being substantially planar when the compression features are pressed together to close the opening between the compression features;
    wherein, the piston, disposed in said housing, comprises (i) an open position, when the head portion does not extend into the fluid port, with the compression features separated to form the opening, and (ii) a closed position, when the head portion extends into the fluid port, with the compression features pressed together to close the opening.

11. The needleless valve system of claim 10, wherein the top surface comprises a depression when the opening is in the open position.

12. The needleless valve system of claim 10, wherein the opening passes through the head portion.

13. The needleless valve system of claim 12, wherein the opening extends along a diameter of the head portion.

14. The needleless valve system of claim 12, wherein the opening is centrally disposed along a center axis of the head portion.

15. The needleless valve system of claim 12, further comprises a bulge disposed along a circumference of the head portion.

16. The needleless valve system of claim 12, wherein in the closed position, the head portion is positioned in the fluid port such that the fluid port is fluidly sealed, and in the open position, the head portion is displaced from the fluid port such that the fluid port is not fluidly sealed.

17. The needleless valve system of claim 10, wherein the housing is configured to engage with a needleless syringe.

18. A needleless valve system comprising:
    a housing comprising a fluid port; and
    a piston having a head portion configured to extend into the fluid port and a base portion, the head portion comprising a continuous top surface and compression features, the top surface being non-planar and the compression features separated to form an opening positioned adjacent the top surface when the head portion is in a relaxed state, and the top surface being substantially planar when the compression features are pressed together to close the opening between the compression features;
    wherein, the piston comprises an open position within said housing, when the head portion does not extend into the fluid port, and the compression features are separated by the opening; and a closed position within said housing, when the head portion is urged by the base portion to extend into the fluid port such that the compression features are pressed together to close the opening.

19. The needleless valve system of claim 18, wherein an outer surface of the head portion is engaged against the fluid port such that the compression features are directed toward the opening in the closed position.

20. The needleless valve system of claim 18, wherein an outer surface of the head portion is separated from an inner surface of the fluid port such that the compression features are unrestrained.

* * * * *